United States Patent [19]
Grendahl et al.

[11] Patent Number: 4,790,845
[45] Date of Patent: Dec. 13, 1988

[54] POSTERIOR CHAMBER LENS

[75] Inventors: Dennis T. Grendahl, Minneapolis, Minn.; Myron E. Lippman, Santa Barbara, Calif.

[73] Assignee: Surgidey Corporation, Goleta, Calif.

[21] Appl. No.: 89,061

[22] Filed: Aug. 27, 1987

Related U.S. Application Data

[62] Division of Ser. No. 316,211, Oct. 29, 1981.

[51] Int. Cl.⁴ .............................................. A61F 2/16
[52] U.S. Cl. ......................................................... 623/6
[58] Field of Search ........................................... 623/6

[56] References Cited

U.S. PATENT DOCUMENTS

| | | | |
|---|---|---|---|
| 4,251,887 | 2/1981 | Anis | 623/6 |
| 4,435,855 | 3/1984 | Pannu | 623/6 |
| 4,473,910 | 10/1984 | Grinder | 623/6 |
| 4,601,720 | 7/1986 | Sinskey | 623/6 |

OTHER PUBLICATIONS

The Simcoe Posterior Chamber Lens, Advertisement Brochure by Cilco, Feb. 1980, 4 pages.
New from Cilco . . . The Single-Piece Perspex Posterior Chamber Lens, Advertisement Brochure, Cilco, Inc. Mar. 1981, 2 pages.

*Primary Examiner*—Ronald L. Frinks
*Attorney, Agent, or Firm*—Hugh D. Jaeger

[57] ABSTRACT

A posterior chamber lens including a plano-convex polymethylmethacrylate (PMMA) optic and two smooth, monofilament, curved, flexible loops attached to and extending from the optic. Each of the loops, also of PMMA, is angulated 10° anteriorly from the plano surface of the optic. The optic is reversed such that the convex surface is posterior and is provided with positioning holes. The PMMA decreasing radius loops and optic provide for a flexible, lightweight and edge-thin lens and loops. The PMMA loops' angulation and plano-convex optic design vault the lens away from the iris. The positioning holes are situated at 12 and 6 o'clock positions and are of a predetermined desired size. A second embodiment of the PMMA lens includes PMMA loops which are substantially parallel to the planar surface of the lens. A third embodiment of the PMMA lens includes PMMA loops which are 10° anteriorly from the convex surface of the optic. A fourth embodiment of the PMMA lens includes closed PMMA loops can be angulated from the surface of the lens. A small loop can be provided at the end of each open loop of decreasing radius. The loop can reverse or fold back and secure to the optic. A geometrical member can be positioned at an end of each loop. One loop can be open and another loop can be closed. The loop can be dialed into position by the junction between one of the loops and the optic.

1 Claim, 6 Drawing Sheets

POSTERIOR CHAMBER LENS

CROSS REFERENCES TO CO-PENDING APPLICATIONS

This application is a division of application Ser. No. 316,211, filed Oct. 29, 1981.

BACKGROUND OF THE INVENTION

1. Field of the Invention

The present invention relates to opthalmological device, or, more particularly, pertains to an implantable posterior chamber lens.

2. Description of the Prior Art

The prior art has known posterior chamber lenses which exhibit unique problems to the patient as well as to the implanting opthalmologist.

One such lens is a single-piece lathe-cut loop and optic. The loops lack true flexibility and are not at an angle to the lens. Machining of lens leaves rough edges, and requires polishing and the use of polishing compounds.

Another such lens lacks the reverse optic effect and lacks thinness at the edge of the optic. The positioning holes further do not ideally lend themselves to implant.

Other prior art lenses utilize more rigid J-loops and large flexible C-loops.

Other types of prior art lenses have loops made of material which tends to dissolve after implant. Other types of prior art lenses utilize optics which are thick and are not lightweight. Finally, other types of prior art lenses are not made of one type of material, but of a combination of materials, which leads to problems after implant.

The present invention overcomes the disadvantages of the prior art by providing a posterior chamber lens with flexible loops at angulation which provide immediate post-insertional centration along the optical axis until capsular fixation occurs. The preferred lens of the present invention is a true reverse optic, made from PMMA material, with desired loop deflection and a thin edge optic providing for a lightweight and flexible posterior chamber lens.

SUMMARY OF THE INVENTION

The general purpose of the present invention is a flexible loop posterior chamber lens manufactured entirely of polymethylmethacrylate (PMMA) where the plano-convex optic is vaulted away from the iris by angulation of the flexible loops with respect to the plano surface of the optic which is a plano-convex reverse optic.

According to one embodiment of the present invention, there is provided a posterior chamber lens including plano-convex polymethylmethacrylate (PMMA) optic and two decreasing radius, smoothly curved, flexible loops angulated anteriorly from the plano surface of the optic whereby the optic is reversed so that the convex surface of the optic is posterior, thereby providing optical and anatomical advantages. The loops are monofilament PMMA material. Two positioning holes are provided through the optic at the 12 and 6 o'clock positions of the optic. The PMMA material of the optic and loops provides for a thin-edge optic, and lightweight and flexible lens.

Another embodiment of the present invention is a posterior chamber lens as described where the loops are in a plane parallel to the planar surface of the optic and join the lens at holes in the edge of the optic.

A further embodiment of the present invention is a posterior chamber lens as described where the loops are angulated to the convex surface of the optic.

An additional embodiment of the present invention is a posterior chamber lens as described where the loops are closed into the lens opposed to being open in the previously described embodiments.

In the first three embodiments as described, a small loop, notch, circle partial circle or angulated deflected member can be attached to the outer end of the decreasing radius member.

In the embodiments, a geometrical member such as a sphere or a partial sphere can be attached to one end of the loops.

While the embodiments have disclosed the loops as being substantially identical, the loops can be nonidentical in that one loop can be provided which is open and another loop can be provided which is closed.

A significant aspect and feature of the present invention is smoothly curved PMMA loops, the loops being attached to the PMMA optic. The dimensional characteristic of the loops provides for a thin, smooth, flexible loop. The loops are angulated at a preferably ten-degree deflection angle and within a range of zero to fifteen degrees.

Another significant aspect and feature of the present invention is a thin optic. The optic is a true plano-convex with respect to front to back and is denoted as a reverse optic. The optic further has an extremely thin-edge thickness. The curved surface of the optic is substantially aligned to the smoothly curved flexible loops in one embodiment.

A further significant aspect and feature of the present invention is a posterior chamber lens having positioning holes at substantially twelve and six o'clock with respect to where the smooth, flexible PMMA loops secure to the edge of the PMMA optic. Other hole combinations can be utilized as later described.

Having thus described one embodiment of the present invention, it is a principal object hereof to provide a posterior chamber lens having a thin PMMA optic and smoothly curved flexible PMMA loops secured thereto.

One object of the present invention is to provide a posterior chamber lens of the present invention with reversed optic and a 10° deflection of the loops, placing the optic toward the nodal point of the eye.

Another object of the present invention is to provide a lens composed of one material, polymethylmethacrylate,(PMMA) thereby providing edge thinness and light weight. Inherently, the optic and loops of the lens are flexible and smooth.

A further object of the present invention is to provide a lens which has deflected loops with respect to the plano surface, loops with no angular deflection, or deflected loops with respect to the convex surface for the implanting surgeons who desire different style lenses.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
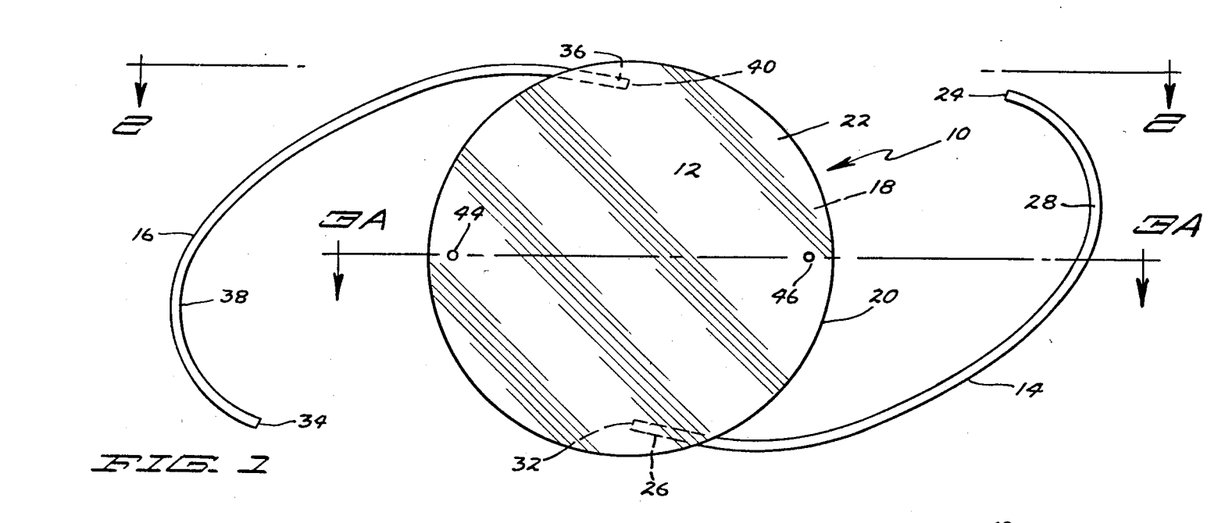
FIG. 1 illustrates a top view of a posterior chamber lens, the present invention.

FIG. 1, which illustrates a top view of a posterior chamber lens 10, the present invention, shows the lens optic 12, a first flexible loop 14 and a second diametrically opposed flexible loop 16 being substantially identical to the loop 14. Both of the loops are frictionally engaged and mechanically secured to the lens optic 12 and both loops are of a like decreasing radius. While a decreasing radius is disclosed, the radius may assume any curved geometrical configuration.

The lens optic 12 includes a plano anterior surface 18, a finite thin edge 20 of 0.05-0.60 mm, preferably 0.33 mm, and a convex posterior surface 22. The lens optic 12 is plano-convex, 4-8 mm in diameter, preferably 6 mm, of polymethylmethacrylate (PMMA) material. The lens optic 12 is a true plano convex with the reversed optic. The lens optic 12 has a range of focal lengths expressed in the range of dioptric powers of 9 to 30, preferably 10 to 27. The lens optic is provided with two smooth, flexible loops 14 and 16. The first loop 14 is now described in detail, with the second loop 16 being identical and a mirror image to the first loop 14. The optic 12 can also be aspheric, convex-convex, or other like optical configuration.

Figures 2, 3A:
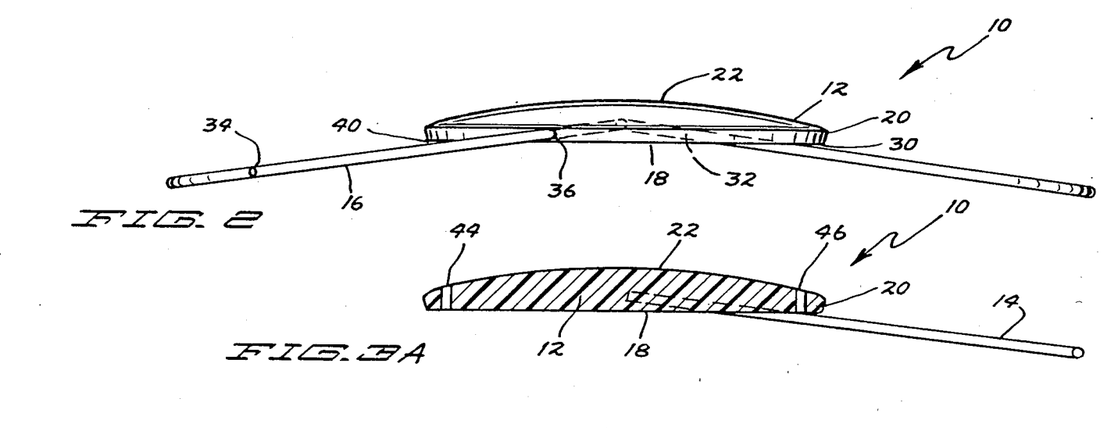
FIG. 2 illustrates a side view of the lens taken along line 2—2 of FIG. 1.
FIG. 3A illustrates a sectional view taken along line 3A—3A of FIG. 1.

The loop 14 is a smooth, flexible, thin, deflected, monofilament, cylindrical member of 0.08 mm to 0.80 mm, preferably 0.127 mm, having a curved, rounded or flat outer end 24. While the member 14 is of a circular cross-section, the cross-section can be ovoid, flattened, or other predetermined geometrical shape. The inner end 26 frictionally and mechanically engages into a hole 32 in the edge 20 of the lens 12, and is subsequently heat staked at an angle 30 as illustrated in FIG. 2, forming a mechanical and chemical bond therebetween. The angle 30 is preferably 10° but can be in the range of 0°-15°. The loop 14 includes a smooth, curved section 28 of decreasing radius between ends 24 and 26.

The identical loop 16 likewise includes a curved rounded or flat outer end 34, an inner end 36, a curved mid-section 38 of decreasing radius, and an angle 40 at a hole 42 where the end 36 is frictionally and mechanically engaged and heat staked into hole 42 at a like angle as loop 14.

Positioning holes 44 and 46 having a preferred diameter of 0.28 mm in a range of 0.05-1 mm are provided at twelve o'clock and six o'clock, by way of example and for purposes of illustration only, and not to be construed as limiting of the present invention. In the alternative, holes can be positioned at eleven and five o'clock positions, eight and two, three and nine, or in any combinations of four holes.

FIG. 2 illustrates a side view of the posterior chamber lens 10 of the present invention where all numerals correspond to those elements previously described. Particular attention is pointed out to the angles 30 and 40 of the deflected loops with respect to the planar surface 18 of the optic 12. The loops 14 and 16 engage the edge 20 of the optic 12 through holes 36 and 32 respectively.

FIG. 3A illustrates a sectional view taken along line 3—3 of FIG. 1 where all numerals correspond to those elements previously described. Attention is pointed to the positioning holes 44 and 46.

The lens optic 12 and the loops 14 and 16 are manufactured by known processes. Depending upon the circumstances, the positioning holes can be eliminated depending upon a surgeon's preference.

Figures 3B, 3C, 3D:
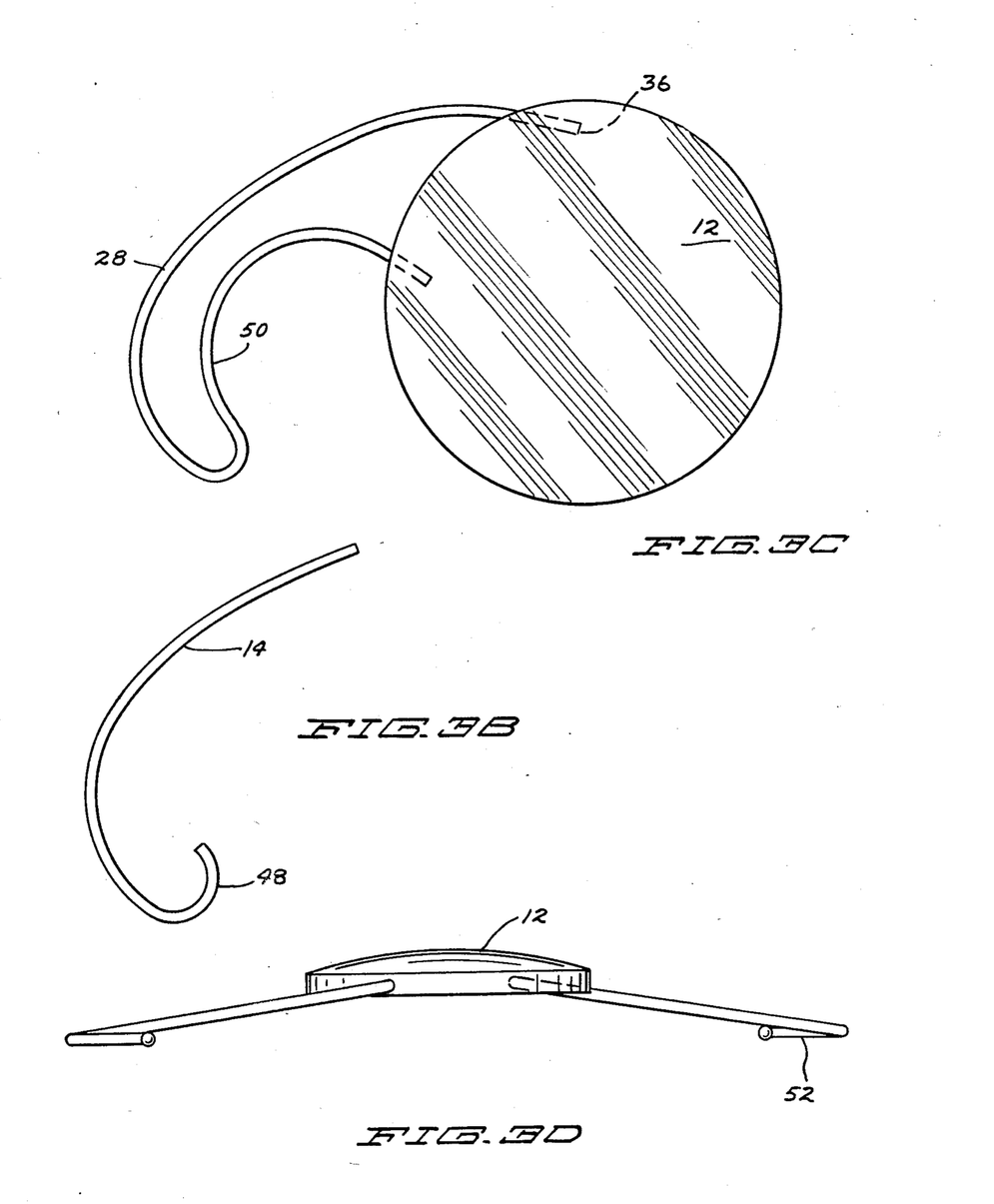
FIG. 3B illustrates a top view of an end of an open decreasing radius loop including an angulated end or small loop end.
FIG. 3C illustrates a top view of a closed loop which folds back and reverse on itself.
FIG. 3D illustrates a sphere or partial sphere attached to one end of the loop.

FIG. 3B illustrates a top view of an end of the open decreasing loop 14 including an angulated end or small loop 48 depending upon the geometrical configuration at the end 24. The length is in the range of 0.1-1 mm and can be anywhere from a slight angular deflection to a small loop 48 having a slight radius. The small loop 48 is connected to the end of loop 14 and likewise, a small loop would also be connected to the loop 16. The angulated end can also assume the geometrical shape of a notch, circle, partial circle, or other like geometrical configuration.

FIG. 3C illustrates a top view of a closed loop which loops around a portion of the optic, folds back inside, and affixes to the edge of the optic in spaced relation to the other end of the loop. At least one loop can be provided on the optic, and possibly two or more loops can be provided on the optic. The FIG. shows the ends at the 9 and 11 o'clock positions. The closed loop of FIG. 3C comprises a filament of PMMA having two spaced ends affixed substantially adjacent to each other to the edge of the optic with the filament being predisposed from a first fixed end 36 to define a first curvature 28, which curves in a first direction spaced outwardly about the periphery of the optic and then reverses along a free end in a fold back to define a second curvature 50 of a lesser radius than the first curvature 28 in a second direction to define an outer free terminal end protrusion and an indentation. The distance between the first curvature 28 and second curvature continuously decreases in direction towards the terminal end protrusion between the edge of the optic and the fold back throughout a majority of its length.

FIG. 3D illustrates a side view of a loop with a sphere or a partial sphere at the end. The sphere 52 provides support for the end of the loop, whether the loop is that of FIGS. 1–3A, 3B, or 3C. The sphere can assume any other predetermined geometrical shape as so desired and predetermined. The sphere or partial sphere can be used on either an open or closed loop.

PREFERRED MODE OF OPERATION

The posterior chamber lens 10 is designed to utilize current surgical processes in lens implantation. The implant lens incorporates the 6 mm. plano-convex polymethylmethacrylate (PMMA) optic attached to the smoothly curved flexible PMMA loops 14 and 16. The entire lens is manufactured and formed from PMMA, a material with a long history, of safety and efficacy, by known processes.

The loops 14 and 16 are angulated 10° anteriorly from the plano surface 18 of the optic, and the optic reversed such that the convex surface 22 is posterior. This design provides multiple optical and anatomical advantages. In order to minimize magnification, an intraocular lens should be placed in a manner which approximates that of the normal lens. This position can be most closely approximated by implanting a posterior chamber lens with angulated loops and reversing the optic such that the plano surface is anterior and the convex surface posterior. This moves the principal refractive plane of the lens 10 implant as far posterior as possible.

Optical design criteria have ideally provided a retinal image with the minimum residual spherical aberration, chromatic aberration, induced aberrational astigmatism and magnification. For a PMMA lens 10, the ideal lens shape is a biconcave meniscus with the flatter surface anterior and the lens design which most closely approximates this criteria is a plano-convex lens 10 with the plano surface 18 anterior. This lens design is similar to the phakic eye where the anterior surface of the natural lens is nearly flat and the posterior surface more convex. Of course, the lens can also assume geometrical shapes of aspheric, convex-convex, concave-concave, and other like optical configurations.

Figure 4:
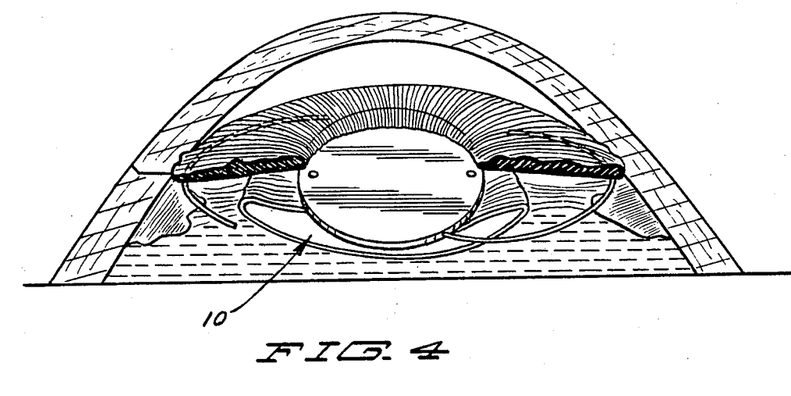
FIG. 4 illustrates ciliary sulcus fixation of the lens of FIG. 1.
Figure 5:
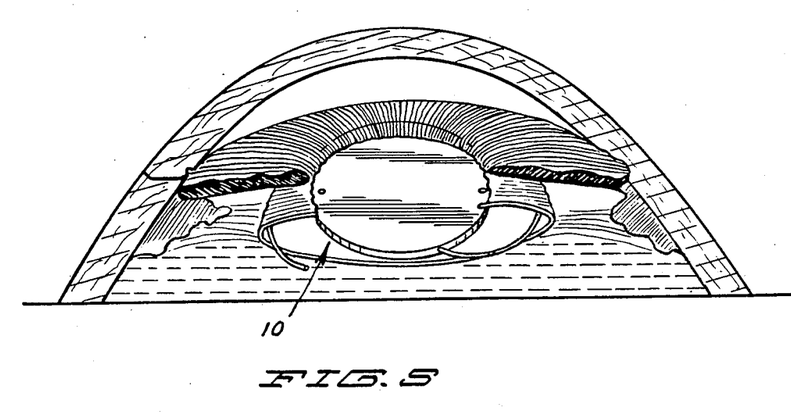
FIG. 5 illustrates capsular bag fixation of the lens of FIG. 1.

To achieve the best visual result, the lens 10 implant must be centered on the optical axis and fixed in position. Immediate post-insertional centration along the optical axis is achieved by the symmetrical, flexible, curved loops 14 and 16 which impact either the ciliary sulcus of FIG. 4, the capsular bag of FIG. 5, or the combination. These loops provide the initial centration until capsular fixation occurs. Permanent physiologic fixation is obtained in the lens 10 by broad capsular fixation to the convex posterior surface of the implant and loops 14 and 16. Additional fixation is often achieved through adhesion of the peripheral loop to the capsular fornices or ciliary sulcus tissue. The loops therefore provide both an initial means of centration and a permanent backup fixation if capsular fixation is not achieved.

The loops 14 and 16 of the lens 10 are flexible enough to prevent striae from forming on the posterior capsule when implantation in the capsular bag is performed. Flexible loops which prevent striae are preferred since striae have been noted clinically to occasionally lead to a fibrous metaplasia of the lens epithelial cells and accelerated opacification of the posterior capsule. Adherence of the lens to the capsular bag occurs with this configuration of FIG. 4 and FIG. 5 preventing free contact with capsular epithelium and also preventing fibrous metaplasia and early opacification of capsule and also by virtue of us conduct with capsule.

The 10° angulation of the loops and plano-convex optic design vault the lens optic 12 away from the iris such that there is reduced contact between the implant and the iris pigment epithelium.

The smoothly curved loop design of the lens is a comfortable compromise between the more rigid J-loops and the larger flexible C-loops. The lens 10 can be placed either in the sulcus or in the bag and it can be implanted using superior loop compression, inferior loop compression, or dialing techniques.

The optic and loops of the lens 10 are manufactured 100% of PMMA. This material is utilized for the lens implant because PMMA has the longest history of tolerance and permanence in ocular tissue. It is not biodegradable, is no affected by ultraviolet light and induces minimal, if any, inflammatory response. The loops 14 and 16 have good memory, sufficient strength and are quite flexible. Inherently, the lens provides a certain spectrum of ultraviolet absorption due to the characteristics of the PMMA material of the optic 12 of the lens 10. Inherently, based on the use of PMMA, the ultraviolet light absorbers filter a larger percentage of light less than 400 nanometers in wavelength. The larger radius of the loop makes contact with a larger area of either the sulcus or the bag.

SURGICAL OPERATIVE PROCEDURE

The following is the procedure for cataract extraction and implantation of the posterior chamber lens. The principles set forth are adapted by each individual surgeon to provide a safe, effective procedure using instruments and techniques with which the surgeon is familiar.

Patient Preparation

The patient is carefully evaluated preoperatively and the appropriate operative procedure—intracapsular cataract extraction, extracapsular cataract extraction (ECCE), or phacoemulsification (PE)—is selected. If ECCE or PE is selected and the patient is then-deemed a candidate for lens implantation, the posterior chamber lens is the primary lens of choice.

An endothelial cell evaluation is obtained through slit lamp specular reflection or endothelial photomicrography. The lens power is selected using A-scan and the Sanders-Kraff-Retzlaff power formulas, and then compared with past refractive data.

Preoperative medication includes 2.5% neosynephrine and 1.0% cyclogyl each thirty minutes for three doses to achieve maximal dilation of the pupil. If local anesthesia is selected, a long-acting anesthetic (0.75% marcaine) in combination with a short-acting anesthetic (2% xylocaine) is preferred. The intraocular tension is reduced to 5-10 mm. of mercury with massage or a Honan balloon.

The entire operation is carried out under an operating microscope with coaxial illumination. Forearm or wrist rests are preferred if available. During the skin preparation, special care is taken to avoid contact to the corneal surface with detergents which can significantly impair the view of the anterior chamber during surgery. A lid speculum such as the Kratz or Jaffe style is used to allow free access to the globe over the superior brow. Superior and inferior rectus bridle sutures of 4-0 silk are placed at the insertion of the superior and inferior rectus muscle. These sutures allow positioning and fixation of the eye during the operation.

A superior fornix based peritomy is performed and careful hemostasis obtained with the wet field cautery. A one-half depth scleral groove is formed 1.0 to 1.5 mm. posterior to the surgical limbus. This groove is 7 mm. in length for PE and 11 mm. for ECCE. The incision is arced toward the cornea such that the peripheral extent of the incision more closely approximates the surgical limbus. Initially, a 1.5 mm. puncture wound is made at eleven o'clock beginning at the base of the scleral groove and extending parallel to the iris to enter the anterior chamber. The internal and external diameter of this incision should be equal. In PE, a 1.0 mm. puncture wound at the two o'clock limbal arcade will allow access to the anterior chamber for a second instrument during the emulsification and lens implantation. For ECCE, this extra incision is unnecessary since a second instrument can be passed through the peripheral extent of the wound.

In patients who are suspected of having a compromised endothelial reserve from the preoperative evaluation, the anterior chamber, is immediately constituted with Healon. A 500 mm. bottle of balanced salt solution warmed to 37° is hung 24 inches above the patient's eye. Parenteral intracardiac adrenaline (1:1000) 0.3 to 0.5 cc. may be added to this solution to assist in maintaining pupillary dilation during the operative procedure.

Using an irrigating cystotome, a can opener anterior capsulectomy is performed. The twelve o'clock portion of the capsule is torn first, and then small contiguous tears are formed extending from the twelve o'clock position to the six o'clock position on each side. Capsulectomy is completed at the six o'clock position. The tears should be radial toward the center of the pupillary space to avoid extension of a capsular tear beyond the area of the zonular attachments. If sulcus fixation is planned, as much anterior capsule as possible is removed. If capsular fixation is preferred, a slightly larger anterior capsular flap is retained.

The incision is then increased to 3 mm. for phacoemulsification or 11 mm. for nucleus expression. The incision can be completed with knife, keratome or scissors, and an attempt is made to maintain a two-plane morticed incision. The nucleus is expressed or emulsified. If the nucleus has been expressed, the incision is closed to 7 mm. with three to four interrupted 10-0 nylon sutures, and an 8-0 black silk is placed at twelve o'clock and tied with a temporary knot. This creates two 3.5 mm. ports for irrigation-aspiration and prevents collapse of the anterior chamber during cortex removal.

The cortex is now removed with a coaxial irrigation aspiration tip to strip and aspirate the cortex. The surgeon may prefer a coaxial cannulae with a 0.3 mm. aspiration port size and a closed chamber. If at any time the pupil becomes too miotic, it may be enlarged by injecting ½ ml. of a 1 to 10,000 dilution of adrenaline into the anterior chamber. After the cortex has been removed, the capsular fornices are inspected with the irrigating Graether collar button or Kuglen push-pull to assure no residual cortex remains. The posterior capsule is then polished or vacuum cleaned.

The incision is opened to 7 mm. by untieing the temporary black silk after ECCE or enlarging with scissors or knife following PE.

Lens Implantation

The lens 10 is grasped-across the optic edge with a Kelman-McPherson forceps or any smooth lens implant forceps. The anterior chamber is constituted with air, fluid or Healon depending upon the surgeon's preference. The lens optic may be coated with Healon also.

The inferior loop is inserted through the incision and into the pupil. The inferior loop is directed to the appropriate angle to either pass between the iris and over the inferior anterior capsular flap for sulcus fixation of FIG. 4, or into the capsular bag, if bag fixation is preferred of FIG. 5. The optic is then teased behind the pupil with a Sinskey hook.

The superior loop may be inserted by a variety of techniques. If the pupil is relatively dilated, the superior loop is grasped near its end with a Kelman-McPherson forceps and compressed inferiorly. The loop forms an elbow which may be placed under direct visual control into the superior sulcus or capsular bag depending on surgeon preference. If the pupil has constricted, it is helpful to retract the superior iris with a second McPherson's forcep or micro-iris hook during superior loop placement.

Alternatively, the lens may be positioned by descending the lens optic towards six o'clock with a positioning hook in the twelve o'clock hole. This compresses the inferior loop and the superior loop is placed behind the iris. Once again, it is often helpful to retract the superior iris with a second instrument.

A popular technique is the dialing technique. In particular, if the pupil is small or the vitreous bulging, the superior loop may be placed in the superior angle and the incision closed partially or completely to allow maintenance of the chamber. The iris is retracted at the one to two o'clock position with a micro-iris hook and the lens is dialed into place by rotating with a positioning hook in the twelve o'clock optic hole. Pressure is directed slowly toward six o'clock and the lens is rotated clockwise behind the peaked pupil.

Finally, the superior loop may be dialed posterior to the iris by using the Graether collar button. The lens optic is stabilized with a positioning hook during this procedure.

The positioning holes and the soft flexible loops which curve continuously from the lens optic facilitate these maneuvers and minimize the dangers of zonular, capsule or iris damage.

Using the positioning holes 44 and 46, the lens is rotated to the horizontal. This may reduce the incidence of certain post-operative complications such as sunset syndrome, large eye sizing problems, updrawn lens, iris tuck, decentration, etc. The optic should be centered in the pupillary space. By tapping over the sclera in the area of the loops, the surgeon can determine whether the lens is in the sulcus or capsular bag. While it is preferred that both loops be either in the ciliary sulcus or in the capsular bag, only a small decentration will occur if this symmetrical implantation is not achieved. A small peripheral iridectomy is performed at twelve o'clock in most cases. The chamber is constituted with fluid. The lens 10 can also be rotated by utilizing the angle between the edge 20 of the lens 10 and the loops 14 and 16.

The central 6.5 to 7.0 mm incision is closed with a running shoelace suture of 10-0 nylon. This suture is adjusted using the Terry keratometer until 1.5 to 2.0 diopters of with the rule astigmatism over the preferred final result is achieved.

If a primary discission is to be performed, a sharp #30 hooked needle is prepared with the tip bent toward the bevel. It is placed on a 3 cc or tuberculin syringe one-half filled with balanced salt solution or attached to the Cavitron hand piece. The chamber is constituted with air, fluid or Healon depending on surgeon preference. The needle is passed sideways through the incision and iridectomy or through the incision and over the iris. It is carefully guided under the lens optic. Gentle irrigation during insertion of the discission needle will help to maintain the chamber and create a space between the optic and posterior capsule. It is guided between the lens optic and posterior capsule until it is ½ mm. inside the lower edge of the optic. Irrigation is stopped and the capsule allowed to float anterior to engage the needle. The capsule is torn toward the incision for approximately four millimeters. Before removal, the needle is turned sideways and passed up and over the lens optic or iridectomy in order to remove any adherent vitreous strand. Miochol is gently instilled into the anterior chamber to achieve miosis. Any retained air or excessive Healon is removed using an aliquot technique. Twenty milligrams of gentamycin sulfate, fifty milligrams of a cephalsporin and three milligrams of celestone soluspan are injected into subconjunctival space and the eye is dressed with a patch and shield.

Postoperative Care

Topical antibiotic and steroid drops are instituted on the first postoperative day and tapered over four to twelve weeks according to the inflammatory responses. The pupil is not routinely dilated unless specifically indicated by inflammation or aynechiae. Pupillary dilation may be performed at any postoperative visit to examine the fundus.

If a primary discission is not performed and late capsular opacification occurs, secondary discission may be performed with a discission knife or disposable needle passed through the limbus or pars plana depending on surgeon preference. The postoperative retinal complications of this secondary procedure may be reduced if capsulotomy is not performed before twelve months postoperative.

DESCRIPTION OF A SECOND EMBODIMENT

Figure 6:
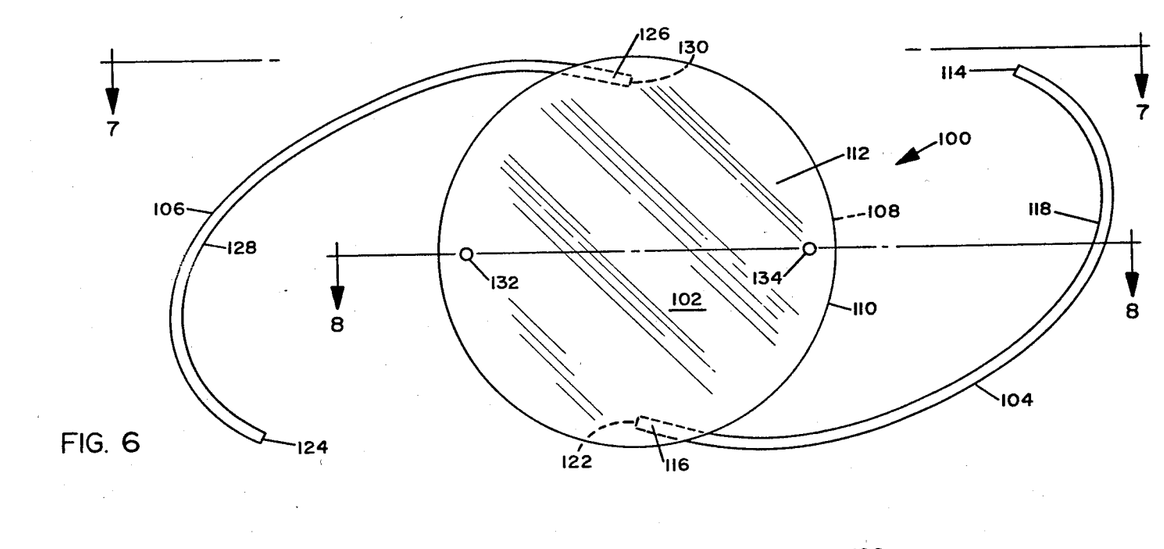
FIG. 6 illustrates a top view of s second embodiment of a posterior chamber lens.

FIG. 6, which illustrates a top view of a posterior chamber lens 100, the second embodiment of the present invention, shows the lens optic 102, a first flexible loop 104 and a second diametrically opposed flexible loop 106 being identical to the loop 104. Both of the loops are frictionally engaged and mechanically secured to the lens optic 102 and both loops are of a like decreasing radius.

The lens optic 102 includes a plano anterior surface 108, a finite thin edge 110 in the range of 0.05 mm to 0.60 mm, and a convex posterior surface 112. The lens optic 102 is a 6 mm plano-convex optic of polymethylmethacrylate (PMMA) material. The lens optic 102 is a true plano-convex with the reversed optic. The lens optic 102 has a range of focal lengths expressed in the range of dioptric powers of 9 to 30, preferably 10 to 27. The lens optic is provided with the two smooth, flexible loops 104 and 106. The first loop 104 is now described in detail, with the second loop 106 being identical to the first loop 104. The diameter of the optic 12 can range from 4-8 mm.

The loop 104 is a smooth, flexible, thin, monofilament, cylindrical member of 0.127 mm having a curved, rounded or flat outer end 114. An inner end 116 frictionally and mechanically engages into a hole 122 in the edge 110 of the lens 102 and is subsequently heat staked. The loop 104 includes a smooth, curved section 118 of decreasing radius between ends 114 and 116. The end forms a mechanical and chemical bond.

The identical loop 106 likewise includes a curved rounded or flat outer end 124, an inner end 126, and a curved mid-section 128. The end 126 frictionally and mechanically engages and is heat staked into hole 130.

Positioning holes 132 and 134 having a diameter of 0.28 mm are provided at twelve o'clock and six o'clock, by way of example and for purposes of illustration only, and not to be construed as limiting of the present invention. The hole diameters can be in a range of 0.20-1.00 mm.

Figure 7:
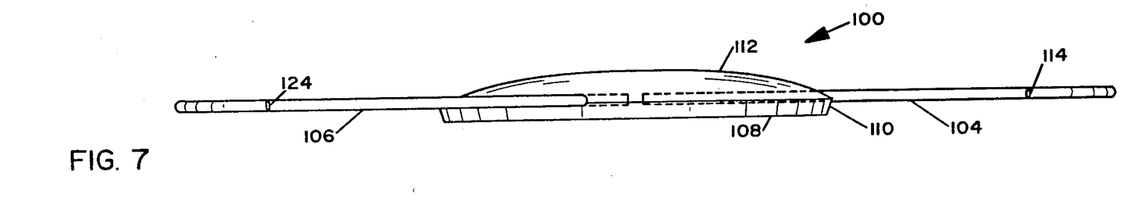
FIG. 7 illustrates a side view taken along line 7—7 of FIG. 6.

FIG. 7 illustrates a side view of the posterior chamber lens 10 of the present invention where all numerals correspond to those elements previously described. It is noted that loops 104 and 106 are substantially parallel to the planar surface 108.

Figure 8:
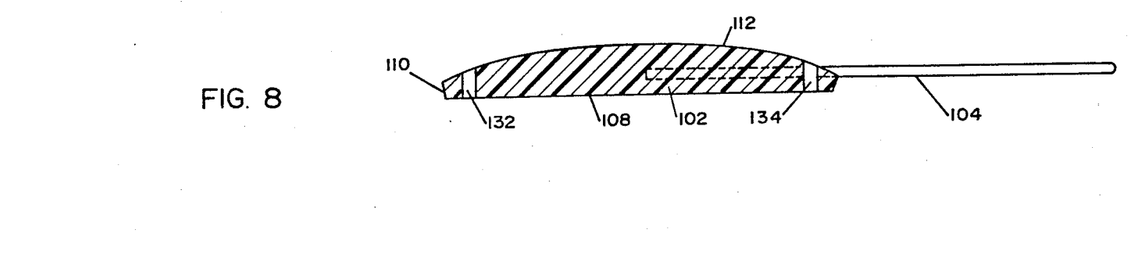
FIG. 8 illustrates a sectional view taken along line 8—8 of FIG. 6.

FIG. 8 illustrates a sectional view taken along line 8—8 of FIG. 6 where all numerals correspond to those elements previously described. Attention is drawn to the positioning holes 132 and 134.

The lens 100 is implanted in a like manner as previously described for FIGS. 1-5.

DESCRIPTION OF A THIRD EMBODIMENT

Figure 9:
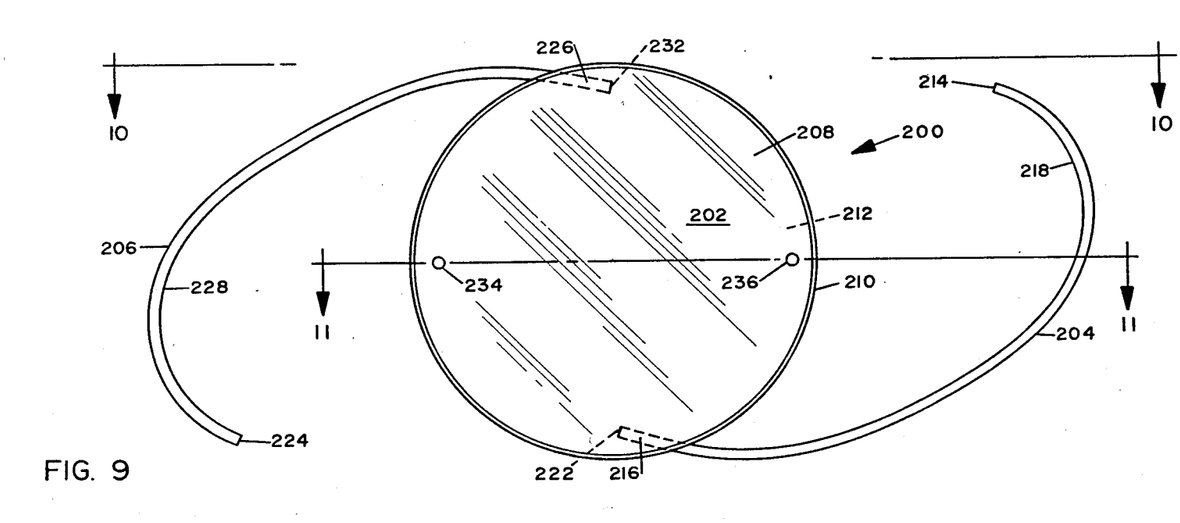
FIG. 9 illustrates a top view of a third embodiment of a posterior chamber lens.

FIG. 9, which illustrates a top view of a posterior chamber lens 200, the third embodiment of the present invention, shows the lens optic 202, a first flexible loop 204, and a second diametrically opposed flexible loop 206 being identical to the loop 204. Both of the loops are frictionally engaged and mechanically secured to the lens optic 202 and both loops are of a like decreasing radius.

The lens optic 202 includes a plano anterior surface 208, a finite thin edge 210 in a range of 0.05 mm to 0.60 mm and a convex posterior surface 212. The lens optic 202 is a 6 mm plano-convex optic of polymethylmethacrylate (PMMA) material. The lens optic 202 is a plano-convex optic. The lens optic 202 has a range of focal lengths expressed in the range of dioptric powers of 9 to 30, preferably 10 to 27. The lens optic is provided with the two smooth, flexible loops 204 and 206. The first loop 204 is now described in detail, with the second loop 206 being identical to the first loop 204. The diameter of the optic 12 can range from 4-8 mm.

Figure 10:
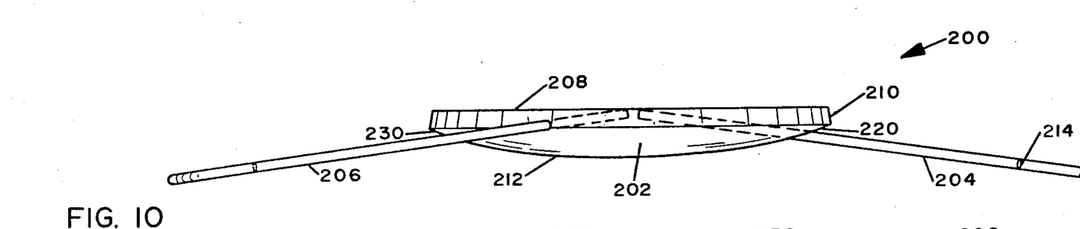
FIG. 10 illustrates a side view taken along line 10—10 of FIG. 9.

The loop 204 is a smooth, flexible, thin, deflected, cylindrical member of 0.127 mm having a curved, rounded or flat outer end 214. An inner end 216 frictionally and mechanically engages into a hole 222 in the edge 210 of the lens 202 and is subsequently heat staked and at an angle 220 as illustrated in FIG. 10. The angle 220 is preferably 10° but can be in the range of 0°-15°. The loop 204 includes a smooth, curved section 218 of decreasing radius between ends 214 and 216. The end forms a mechanical and chemical bond.

The identical loop 206 likewise includes a curved outer end 224, an inner end 226, a curved mid-section 228, and an angle 230 at a hole 232 where the end 226 is frictionally and mechanically engaged and heat staked into hole 232.

Positioning holes 234 and 236 having a diameter of 0.28 mm are provided at twelve o'clock and six o'clock, by way of example and for purposes of illustration only, and not to be construed as limiting of the present invention. The hole diameters can be in a range of 0.20–1.00 mm.

FIG. 10 illustrates a side view of the posterior chamber lens 200 of the present invention where all numerals correspond to those elements previously described. Attention is drawn to the angles 220 and 230 which are greater than ninety degrees with respect to the planar surface 208.

Figure 11:
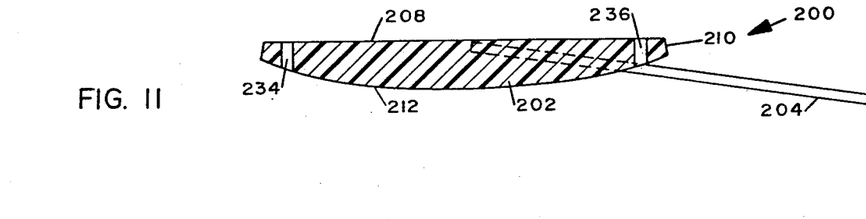
FIG. 11 illustrates a sectional view taken along line 11—11 of FIG. 9.

FIG. 11 illustrates a sectional view taken along line 11—11 of FIG. 9 where all numerals correspond to those elements previously described.

The lens 200 is implanted in a like manner as previously described for FIGS. 1-5.

DESCRIPTION OF A FOURTH PREFERRED EMBODIMENT

Figure 12:
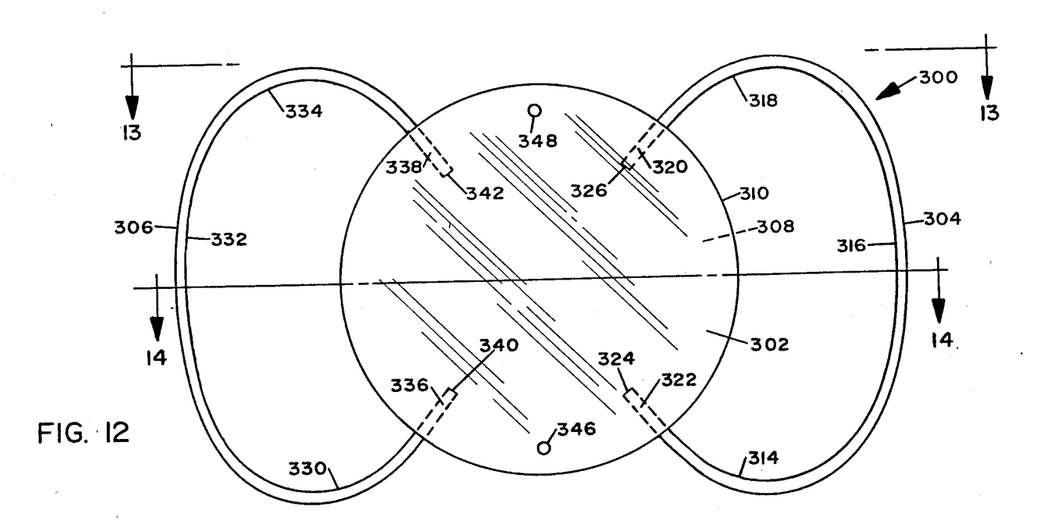
FIG. 12 illustrates a top view of a fourth embodiment of a posterior chamber lens with the closed loops.

FIG. 12, which illustrates a top view of a posterior chamber lens 300, the fourth embodiment of the present invention shows the lens optic 302, a first flexible closed loop 304 and a second diametrically opposed closed flexible loop 306 being identical to the loop 304. Both of the loops are frictionally engaged and mechanically secured to the lens optic 302 through holes in an edge of the optic 302. Both loops 304 and 306 are of like radiuses.

The lens optic 302 includes a plano anterior surface 308, a finite thin edge 310 and a convex posterior surface 312. The lens optic 302 is a plano-convex optic of polymethylmethacrylate (PMMA) material. The lens optic 302 is a plano-convex optic. The lens optic 302 has a range of focal lengths expressed in the range of dioptric powers of 9 to 30, preferably 10 to 27. The lens optic is provided with the two smooth, flexible closed loops 304 and 306. The first loop 304 is now described in detail, with the second loop 306 being identical to the first loop 304.

Figures 13, 14:
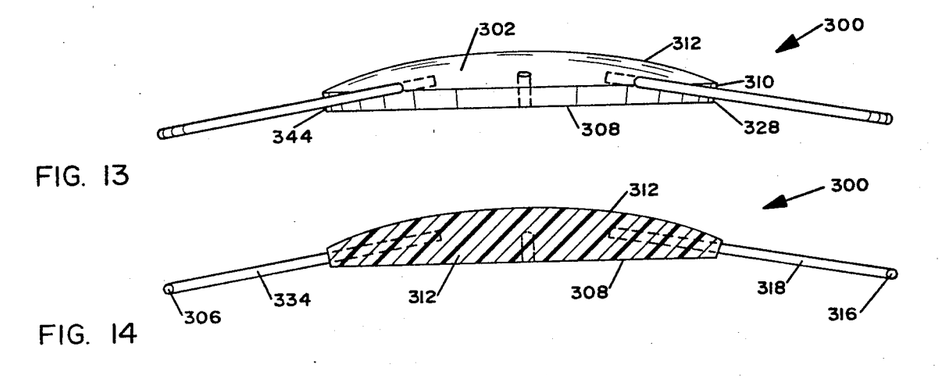
FIG. 13 illustrates a side view taken along line 13—13 of FIG. 12.
FIG. 14 illustrates a sectional view taken along line 14—14 of FIG. 12.

The first loop 304 is a smooth, flexible, thin, cylindrical member of decreasing radius 314, a large radius 316, and a decreasing radius 318. Inner ends 320 and 322 frictionally and mechanically engage into a hole 324 and 326 in the edge 310 of the lens 302 and is subsequently heat staked and at an angle 328 as illustrated in FIG. 13. The angle 328 is preferably 10° but can be in the range of 0°–15°. The loop 304 includes a smooth curved section 316 of large radius between the decreasing radiuses 314 and 318.

The identical closed loop 306 likewise includes radiuses 330, 332 and 334 respectively, ends 336 and 338, and holes 340 and 342, and an angle 344 as illustrated in FIG. 13.

Positioning holes 346 and 348 are provided at twelve o'clock and six o'clock positions by way of example and for purposes of illustration only, and not to be construed as limiting of the present invention.

The size of the optic 302 and the cross section of the loops are identical to those discussed for FIGS. 1-3. The size of the loops are dependent upon a number of factors including the diameter of the lens and the size of the implant. Inherently, the size of the loops including the overall length of each of the closed loops is proportional to the diameter of the optic 302. The radius of the decreasing radiuses and the large radius is again proportional to the size of the diameter of the optic 302.

FIG. 13 illustrates a side view of the lens where all numerals correspond to those elements previously described. The angulation of the loops 304 and 306 are shown which can be in the range of 0°–15°, while the angle of 10° is preferred.

FIG. 14 illustrates a sectional view taken along line 14—14 of FIG. 12 where all numerals correspond to those elements previously described. Location of the positioning hole 340 is noted as being referenced at the 12 o'clock position.

Additional alternative embodiments are now described. The lens optic can be aspheric, convex-convex, or convex-concave while plano-convex is preferred. While the free ends of the loops are disclosed in FIGS. 1-11, each of the ends of the loops can be closed by bonding either the end to the optic or to a portion of the curved radius of the loop with the end to the optic being illustrated in FIGS. 12-14.

Other two- or multi-structure configurations are within the scope of this invention. While loops of curved radius have been disclosed, other predetermined geometrical configurations can also be utilized within the teachings of this invention. The loops can be different in lieu of being identical.

The lens optic can be of second material while the loop structures are of PMMA. The loops can be a combination of materials.

The loops can be an integral member of the optic or can be assembled to the lens optic as disclosed. While the loops have been illustrated as round cylindrical members, the loops can also be ribbon or strands, and can be produced simultaneously, or simultaneously with the lens, or assembled individually to the lens.

The material of the loops can be a polymer, or like material. Each of the loops can be a cylinder, ovoid, ribbon, strand, flat rectangular member, or other member of a predetermined geometrical configuration and shape. While the loop is made out of PMMA, the optic can be made out of a second material as so determined. The advantage of PMMA is the flexibility and as an implant material and lack of inflamatory response of the eye. The PMMA does not activate the complement pathway involved in inflammatory response.

The positioning holes of the optic can be eliminated as the lens can be dialed into position by the surgeon by inserting a surgical tool between the junction of the optic such as the edge of the optic and one of the loops whether the loop be an open loop or a closed loop.

The lens optic and loops, either open or closed, can be manufactured from a single piece of PMMA by known processes. The loops or the optic can be colored for ease of identification. The PMMA material is hypoinflammatory in the eye and is nonbiodegradable.

The loops can be manufactured as composite materials as PMMA and other materials simultaneously or as an assembled combination of the materials. Such an example would be PMMA over a core of a second material or woven with a second material. The composites could include a plurality of geometrical shapes either solely or in combination, those shapes including but not limited to strands, ribbons, flat members, cylindrical members, ovoid, oval, by way of example and for purposes of illustration and not to be construed as limiting of the present invention. The composites can be produced and bundled so ultaneously and attached to the optic; or, produced separately, subsequently assembled, and then attached to the optic, or variations thereof. Particularly, the composites could be monofilament composited of any configuration such as an inner or outer wrap produced in line, or an inner wrap or outer wrap assembled at a later time to the optic. The composites can be bundled concurrently with other composites to form larger bundles of a member. The composites and bundles can be produced separately or simultaneously by the known processes, and later assembled to the optic.

Each of the small diameter monofilament members can be produced concurrently with other members to form a larger bundle member.

Each of the small diameter monofilament members can be produced separately and later assembled to form larger bundle members. The bundles can be subsequently attached to the optic.

Based on the use of PMMA materials for each of the flexible loops where each loop has a predetermined geometrical radial configuration, the resultant loop is flexible and smooth. The resultant smooth loop is so smooth that further processes such as polishing are not required which also applies to the optic.

The number of holes and positioning holes are dependent upon the particular configuration of the loops about the optic. While the positioning holes have been illustrated as protruding through the lens, the positioning holes can only extend partially into the optic.

The number of loops about the optic, the radial configuration about the optic, and the end radial configuration at the loops can assume relative permutations in light of this patent. Any plurality of geometrical configurations are within the scope of this patent including three, four, five, six, etc. loop configurations. Embodiments such as an "X","Y", a penta or a hex formation, etc. are within the scope of this patent as well as other geometrical configurations.

Various modifications can be made to the present invention without departing from the apparent scope thereof.

Having thus described the invention, what is claimed is:

1. A posterior chamber lens implant for the human eye for use after extracapsular surgery in which a posterior capsule is left substantially intact, said lens implant comprising:
    a. a substantially circular PMMA optic having a plano anterior surface, a convex posterior surface and a substantially circular and continuous outer edge; and,
    b. two opposed loops, each loop comprising a filament of PMMA having two ends affixed substantially adjacent to each other and to said edge of said optic, each of said filament being predisposed to define a first curvature which curves in a first direction and reverses along a free end in a fold back to define a second curvature of a lesser radius than said first curvature in a second direction to thereby define an outer terminal end protrusion and an indentation, the distance between said first curvature and said second curvature continuously decreasing in a direction towards said terminal end protrusion between said edge of said optic and said fold back throughout a majority of its length, said loops being adapted to secure said optic to the eye within the posterior chamber, each of said loops affixed to said optic at an angle of about 15° anterior to said convex posterior surface such that said convex posterior surface is caused to abut against the posterior capsule.

* * * * *